(12) United States Patent
Mizuguchi et al.

(10) Patent No.: US 10,058,528 B2
(45) Date of Patent: *Aug. 28, 2018

(54) COMPOSITIONS AND METHODS FOR TREATING NON-ALCOHOLIC STEATOHEPATITIS

(71) Applicant: MOCHIDA PHARMACEUTICAL CO., LTD., Tokyo (JP)

(72) Inventors: Kiyoshi Mizuguchi, Tokyo (JP); Tsuyoshi Harada, Tokyo (JP); Atsushi Osada, Tokyo (JP); Hiroyuki Kawano, Tokyo (JP); Masayuki Ichioka, Tokyo (JP)

(73) Assignee: MOCHIDA PHARMACEUTICAL CO., LTD. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/269,134

(22) Filed: Sep. 19, 2016

(65) Prior Publication Data

US 2017/0007566 A1    Jan. 12, 2017

Related U.S. Application Data

(63) Continuation of application No. 14/435,121, filed as application No. PCT/JP2012/006551 on Oct. 12, 2012, now Pat. No. 9,486,433.

(51) Int. Cl.
  *A61K 31/232*  (2006.01)
  *A61K 31/202*  (2006.01)

(52) U.S. Cl.
  CPC .......... *A61K 31/232* (2013.01); *A61K 31/202* (2013.01)

(58) Field of Classification Search
  CPC ..................... A61K 31/232; A61K 31/202
  USPC ........................................................ 514/549
  See application file for complete search history.

(56) References Cited

U.S. PATENT DOCUMENTS

| | | | |
|---|---|---|---|
| 3,692,895 | A | 9/1972 | Norman et al. |
| 4,379,785 | A | 4/1983 | Weyer et al. |
| 4,572,912 | A | 2/1986 | Yoshioka et al. |
| 4,579,730 | A | 4/1986 | Kidron et al. |
| 4,639,436 | A | 1/1987 | Junge et al. |
| 4,849,405 | A | 7/1989 | Ecanow |
| 4,904,769 | A | 2/1990 | Rauenbusch |
| 4,963,526 | A | 10/1990 | Ecanow |
| 5,019,508 | A | 5/1991 | Johnson et al. |
| 5,594,016 | A | 1/1997 | Ueno et al. |
| 5,614,492 | A | 3/1997 | Habener |
| 5,642,868 | A | 7/1997 | Talmy et al. |
| 5,703,188 | A | 12/1997 | Mandeville, III et al. |
| 5,763,396 | A | 6/1998 | Weiner et al. |
| 5,824,638 | A | 10/1998 | Burnside et al. |
| 5,843,866 | A | 12/1998 | Parker et al. |
| 6,153,632 | A | 11/2000 | Rieveley |
| 6,191,105 | B1 | 2/2001 | Ekwuribe et al. |
| 6,296,850 | B1 | 10/2001 | Bjoerklund et al. |
| 6,706,488 | B2 | 3/2004 | Bjorklund et al. |
| 6,716,968 | B2 | 4/2004 | Bjorklund et al. |
| 7,883,904 | B2 | 2/2011 | Feldstein et al. |
| 7,897,591 | B2 | 3/2011 | Puder et al. |
| 8,853,256 | B2 | 10/2014 | Yokoyama et al. |
| 9,060,981 | B2 | 6/2015 | Sato et al. |
| 9,486,433 | B2 * | 11/2016 | Mizuguchi ........... A61K 31/232 |
| 2007/0218579 | A1 | 9/2007 | Lee et al. |
| 2008/0311593 | A1 | 12/2008 | Younossi et al. |
| 2009/0297546 | A1 | 12/2009 | Yamada et al. |
| 2011/0082119 | A1 | 4/2011 | Yano |
| 2011/0092592 | A1 | 4/2011 | Yano |
| 2011/0105510 | A1 | 5/2011 | Ishikawa |
| 2012/0065264 | A1 | 3/2012 | Fujii et al. |
| 2012/0231471 | A1 | 9/2012 | Sato et al. |
| 2012/0264824 | A1 | 10/2012 | Mizuguchi et al. |
| 2014/0057981 | A1 | 2/2014 | Fujii et al. |
| 2015/0051143 | A1 | 2/2015 | Harada et al. |
| 2015/0247869 | A1 | 9/2015 | Sato et al. |
| 2015/0258054 | A1 | 9/2015 | Mizuguchi et al. |
| 2016/0030378 | A1 | 2/2016 | Harada et al. |
| 2016/0213639 | A1 | 7/2016 | Suzuki et al. |

FOREIGN PATENT DOCUMENTS

| | | | |
|---|---|---|---|
| EP | 1582873 | A1 | 10/2005 |
| EP | 1782807 | A1 | 5/2007 |
| EP | 2308493 | A1 | 4/2011 |
| EP | 2433630 | A1 | 3/2012 |
| EP | 2490026 | A1 | 8/2012 |
| EP | 2719382 | A1 | 4/2014 |
| JP | 2000102399 | A | 4/2000 |
| JP | 2002114768 | A | 4/2002 |
| JP | 2007236253 | A | 9/2007 |
| JP | 2007315752 | A | 12/2007 |
| JP | 2009120607 | A | 6/2009 |
| JP | 2009534317 | A | 9/2009 |

(Continued)

OTHER PUBLICATIONS

Ahmed, et al., Reno-protective Effects of Eicosapentaenoic Acid (EPA) Against PAN Induced Nephrosis in WKY Rats. Asian J. Biochem., 2012; 7(1): 16-26.
American Diabetes Association and National Institute of Diabetes, Digestive, and Kidney Diseases. The prevention or delay of type 2 diabetes. Diabetes Care. Apr. 2002;25(4):742-9.
Anty, R., A new composite model including metabolic syndrome, alanine aminotransferase and cytokeratin-18 for the diagnosis of non-alcoholic steatohepatitis in morbidly obese patients. Aliment Pharmacol Ther. Dec. 2010;32(11-12):1315-22. doi: 10.1111/j.1365-2036.2010.04480.x. Epub Oct. 7, 2010.
Armutcu, et al. Thymosin alpha 1 attenuates lipid peroxidation and improves fructose-induced steatohepatitis in rats. Clin Biochem. Jun. 2005;38(6):540-7.
Brown, TT. et al., Association between systemic inflammation and incident diabetes in HIV-infected patients after initiation of antiretroviral therapy. Diabetes Care. Oct. 2010;33(10):2244-9. doi: 10.2337/dc10-0633. Epub Jul. 27, 2010.
Capanni, et al. Prolonged n-3 polyunsaturated fatty acid supplementation ameliorates hepatic steatosis in patients with non-alcoholic fatty liver disease: a pilot study. Aliment Pharmacol Ther. Apr. 15, 2006;23(8):1143-51.
Carpentier, et al. n-3 fatty acids and the metabolic syndrome. Am J Clin Nutr. Jun. 2006;83(6 Suppl):1499S-1504S.

(Continued)

*Primary Examiner* — Yevgeny Valenrod
(74) *Attorney, Agent, or Firm* — Wilson Sonsini Goodrich & Rosati

(57) ABSTRACT

Compositions and method are disclosed comprising ethyl icosapentate for use in treatment of non-alcoholic steatohepatis (NASH).

23 Claims, No Drawings

(56) References Cited

FOREIGN PATENT DOCUMENTS

| | | |
|---|---|---|
| JP | 2011006380 A | 1/2011 |
| JP | 2011519846 A | 7/2011 |
| JP | 2012180337 A | 9/2012 |
| WO | WO-8505029 A1 | 11/1985 |
| WO | WO-9711345 A1 | 3/1997 |
| WO | WO-9805331 A2 | 2/1998 |
| WO | WO-9857652 A1 | 12/1998 |
| WO | WO-9958518 A2 | 11/1999 |
| WO | WO-9958521 A1 | 11/1999 |
| WO | WO-9958522 A1 | 11/1999 |
| WO | WO-9961435 A1 | 12/1999 |
| WO | WO-0226707 A1 | 4/2002 |
| WO | WO-0226743 A1 | 4/2002 |
| WO | WO-03032916 A2 | 4/2003 |
| WO | WO-03032982 A1 | 4/2003 |
| WO | WO-03041729 A1 | 5/2003 |
| WO | WO-03055883 A1 | 7/2003 |
| WO | WO-2005063231 A2 | 7/2005 |
| WO | WO-2007016390 A1 | 2/2007 |
| WO | WO-2008075788 A1 | 6/2008 |
| WO | WO-2008113177 A1 | 9/2008 |
| WO | WO-2009028457 A1 | 3/2009 |
| WO | WO-2009151116 A1 | 12/2009 |
| WO | WO-2009151125 A1 | 12/2009 |
| WO | WO-2009154230 A1 | 12/2009 |
| WO | WO-2010004982 A1 | 1/2010 |
| WO | WO-2010134614 A1 | 11/2010 |
| WO | WO-2011046204 A1 | 4/2011 |
| WO | WO-2012032417 A2 | 3/2012 |
| WO | WO-2013127728 A1 | 9/2013 |
| WO | WO-2014057522 A1 | 4/2014 |
| WO | WO-2014142364 A2 | 9/2014 |
| WO | WO-2015053379 A1 | 4/2015 |

OTHER PUBLICATIONS

Chatzigeorgiou, et at. Plasma and urine soluble CD40 (sCD40) in children and adolescents with type 1 diabetes mellitus (T1DM). A possible pathway to diabetic angiopathy. FEBS Journal (2008), vol. 275 (Suppl. 1). PP7A-14, p. 303 (abstract).

Ciprandi, G. et al., Serum adipsin levels in patients with seasonal allergic rhinitis: preliminary data.Int Immunopharmacol. Nov. 2009;9(12):1460-3. doi: 10.1016/j.intimp.2009.08.004. Epub Aug. 20, 2009.

Cleveland Clinic (downloaded online on Feb. 26, 2015 from URL:<http://my.clevelandclinic.org/health/diagnostics/hic-blood-glucose-test>).

Communication Pursuant to Article 94(3) EPC dated May 16, 2014, in European Patent Application No. 10823472.5.

Database Biosis (Online] BioSciences Information Service, Philadelphia. PA, US (Apr. 2006); Gurhen et at, The Effects of Atorvastatin on Hematological and Inflammatory Parameters, 'XP002700442, Database Accession No. PREV200900258247—abstract'.

Database Biosis [Online) BioSciences Information Service, Philadelphia, PA, US (Nov. 2008): Cayon et al, "Gene expression in obese patients with non-alcoholic steatohepatitis," XP002700444, Database Accession No. PREV200800490452 'abstract'.

Dennis. The growing phospholipase A2 superfamily of signal transduction enzymes. Trends Biochem Sci. Jan. 1997;22(1):1-2.

English translation of International Preliminary Report on Patentability and Written Opinion dated Apr. 17, 2012, in PCT International Application No. PCT/JP2010/068168.

Estep, et al. Expression of cytokine signaling genes in morbidly obese patients with non-alcoholic steatohepatitis and hepatic fibrosis. Obes Surg. May 2009;19(5):617-24. doi: 10.1007/s11695-009-9814-x. Epub Mar. 12, 2009.

European search report and opinion dated Mar. 4, 2013 for EP Application No. 12188329.2.

Extended European Search Report dated Jul. 13, 2012, in European Patent Application No. 10823472.5.

Farrell, et al. NASH is an Inflammatory Disorder: Pathogenic, Prognostic and Therapeutic Implications. Gut Liver. Apr. 2012;6(2):149-71. doi: 10.5009/gnl.2012.6.2.149. Epub Apr. 17, 2012.

Feldstein, et al. Hepatocyte apoptosis and fas expression are prominent features of human nonalcoholic steatohepatitis. Gastroenterology. Aug. 2003;125(2):437-43.

Forst, et al. Improved plaque stabilityyand reduced inflammation during pioglitazone treatment in type 2 diabetic patients with CHD. Diabetes. Jun. 2007; vol. 55, Suppl. 1. 647-P, p. A172.

Forst, et al. Pleiotrophic and anti-inflammatory effects of pioglitazone precede the metabolic activity in type 2 diabetic patients with coronary artery disease. Atherosclerosis. Mar. 2008;197(1):311-7. Epub Jun. 22, 2007.

Gomolka, B. et al., Analysis of omega-3 and omega-6 fatty acid-derived lipid metabolite formation in human and mouse blood samples. Prostaglandins Other Lipid Mediat. Apr. 2011;94(3-4):81-7. doi: 10.1016/j.prostaglandins.2010.12.006. Epub Jan. 12, 2011.

Hanniman, et al. Apolipoprotein A-IV is regulated by nutritional and metabolic stress: involvement of glucocorticoids, HNF-4 alpha, and PGC-1 alpha. J Lipid Res. Nov. 2006;47(11):2503-14. Epub Aug. 23, 2006.

Haukeland, et al. Systemic inflammation in nonalcoholic fatty liver disease is characterized by elevated levels of CCL2. J Hepatol. Jun. 2006;44(6):1167-74. Epub Mar. 20, 2006.

Horie et al. Hepatocyte-specific pten deficiency results in steatohepatitis and hepatocellular carcinoma, and Insulin Hypersensitivity. Hepatology, Oct. 2004, No. 609, p. 428A.

Hosoyamada, K. et al., Fatty liver in men is associated with high serum levels of small, dense low-density lipoprotein cholesterol. Diabetol Metab Syndr. Jul. 18, 2012;4(1):34.

International preliminary report on patentability and written opinion dated Nov. 20, 2012 for PCT Application No. JP2012/006551.

International search report and written opinion dated Nov. 20, 2012 for PCT Application No. JP2012/006551.

International search report and written opinion dated Dec. 16, 2014 for PCT Application No. JP2014/077120.

International search report dated Jan. 25, 2011 for PCT/JP2010/068168.

Jeppesen et al, Relation of High TG—Low HDL Cholesterol and LDL Cholesterol to the Incidence of Ischemic Heart Disease (Arteriosclerosis, Thrombosis, and Vascular Biology. 1997; 17: 1114-1120).

Jin et al. Telmisartan prevents hepatic fibrosis and enzyme-altered lesions in liver cirrhosis rat induced by a choline-deficient L-amino acid-defined diet. Biochem Biophys Res Commun. Dec. 28, 2007;364(4):801-7. Epub Oct. 24, 2007.

Johannsson, et al. Growth hormone treatment of abdominally obese men reduces abdominal fat mass, improves glucose and lipoprotein metabolism, and reduces diastolic blood pressure. J Clin Endocrinol Metab. Mar. 1997;82(3):727-34.

Kajikawa, et al. Eicosapentaenoic acid attenuates progression of hepatic fibrosis with inhibition of reactive oxygen species production in rats fed methionine- and choline-deficient diet. Digestive Diseases and Sciences, 201, vol. 56, No. 4, p. 1065-1074.

Kajikawa, et al. Highly Purified Eicosapentaenoic Acid Ethyl Ester Prevents Development of Steatosis and Hepatic Fibrosis in Rats. Digestive Diseases and Sciences, 2010, vol. 55, No. 3, p. 631-641.

Kalhan, SC. et al., Plasma metabolomic profile in nonalcoholic fatty liver disease. Metabolism. Mar. 2011;60(3):404-13. doi: 10.1016/j.metabol.2010.03.006. Epub Apr. 27, 2010.

Kan Tan Sui. 2010, vol. 60, No. 5, p. 759-764.

Kanzo. 2002, vol. 43, No. Supplement 2, p. A397.

Kanzo. 2005, vol. 46, No. Supplement 2, p. A329.

Kanzo. vol. 53, No. Supplement 2, 212, p. A706.

Kawashima, et al. Preventive Effects of Highly Purified Eicosapentaenoic Acid on Development of Steatosis and Hepatic Fibrosis Induced by a Methionine- and Choline-Deficient Diet in Rats. Gastroenterology, 2009, vol. 136, No. 5, p. A804.

Kleinen, et al. Design and validation of a histological scoring system for nonalcoholic fatty liver disease. Hepatology. Jun. 2005;41(6):1313-21.

(56) References Cited

OTHER PUBLICATIONS

Kudo, et al. Lipopolysaccharide triggered TNF-alpha-induced hepatocyte apoptosis in a murine non-alcoholic steatohepatitis model. J Hepatol. Jul. 2009;51(1):168-75. doi: 10.1016/j.jhep.2009.02.032. Epub May 3, 2009.
Kurita et al. Olmesartan ameliorates a dietary rat model of non-alcoholic steatohepatitis through its pleiotropic effects. Eur J Pharmacol. Jul. 7, 2008;588(2-3):316-24. doi: 10.1016/j.ejphar.2008.04.028. Epub Apr. 16, 2008.
Lanfear, DE. et al., Short term effects of milrinone on biomarkers of necrosis, apoptosis, and inflammation in patients with severe heart failure.J Transl Med. Jul. 29, 2009;7:67. doi: 10.1186/1479-5876-7-67.
Lee, et al. Comparison of methods to measure low serum estradiol levels in postmenopausal women. J Clin Endocrinol Metab. Oct. 2006;91(10):3791-7. Epub Aug. 1, 2006.
Lee, H. et al., Diagnostic Significance of Serum HMGB1 in Colorectal Carcinomas. 2012.PLoS One 7(4): e34318. doi:10.1371/journal.pone.0034318.
Lowe, Gdo. et al., Blood viscosity and risk of cardiovascular events: the Edinburgh Artery Study. British Journal of Haematalogy. 1997. 96: 168-173.
Mason, et al. Effect of enhanced glycemic control with saxagliptin on endothelial nitric oxide release and CD40 levels in obese rats. J Atheroscler Thromb. 2011;18(9):774-83. Epub Jun. 13, 2011.
MedIndia (downloaded online on Feb. 25, 2015 from URL:<http://www.medindia.net/patients/patientinfo/hba1c-blood-sugar-test.htm>).
Meigs, et al. The natural history of progression from normal glucose tolerance to type 2 diabetes in the Baltimore Longitudinal Study of Aging. Diabetes. Jun. 2003;52(6):1475-84.
Mitsuhashi, H. [Thrombo test (TBT), hepaplastin test (HPT)]. Nihon Rinsho. Dec. 2004;62 Suppl 12:594-6.
Nakajima, K. et al., The characteristics of remnant lipoproteins in the fasting and postprandial plasma.Clinica Chimica Acta; International Journal of Clinical Chemistry. 2012, 413(13-14):1077-1086.
National Institutes of Health (NIH) National Institute of Diabetes and Digestive and Kidney Diseases, "Nonalcoholic Steatohepatitis", Nov. 2006.
Nemoto, et al. Ethyl-eicosapentaenoic acid reduces liver lipids and lowers plasma levels of lipids in mice fed a high-fat diet. In Vivo. Sep.-Oct. 2009;23(5):685-9.
Neuschwander-Tetri, et al. Nonalcoholic steatohepatitis: summary of an AASLD Single Topic Conference. Hepatology. May 2003;37(5):1202-19.
Nichols, et al. From menarche to menopause: trends among US Women born from 1912 to 1969. Am J Epidemiol. Nov. 15, 2006;164(10):1003-11. Epub Aug. 23, 2006.
Notarnicola, et al. Increased serum levels of lipogenic enzymes in patients with severe liver steatosis. Lipids Health Dis. Oct. 30, 2012;11:145. doi: 10.1186/1476-511X-11-145.
Notice of allowance dated Feb. 20, 2015 for U.S. Appl. No. 13/500,753.
Notice of allowance dated Jul. 25, 2016 for U.S. Appl. No. 14/435,121.
Notification of Reasons for Refusal dated Nov. 4, 2014, in Japanese Patent Application No. 2011-536192, with English translation.
Obstetrical and Gynecological Practice. vol. 56, No. 8, 2007, p. 1161-1165.
Oestvang, et al. PhospholipaseA2: a key regulator of inflammatory signalling and a connector to fibrosis development in atherosclerosis. Biochim Biophys Acta. Nov. 2006;1761(11):1309-16. Epub Jul. 1, 2006.
Office action dated Feb. 11, 2013 for U.S. Appl. No. 13/088,072.
Office action dated Mar. 21, 2014 for U.S. Appl. No. 13/500,753.
Office action dated Apr. 19, 2016 for U.S. Appl. No. 14/775,452.
Office action dated Apr. 27, 2016 for U.S. Appl. No. 14/435,121.
Office action dated May 8, 2015 for U.S. Appl. No. 14/209,964.
Office action dated Jul. 20, 2015 for U.S. Appl. No. 13/088,072.
Office action dated Aug. 13, 2013 for U.S. Appl. No. 13/088,072.
Office action dated Sep. 7, 2016 for U.S. Appl. No. 14/775,452.
Office action dated Sep. 11, 2015 for U.S. Appl. No. 14/209,964.
Office action dated Oct. 6, 2016 for U.S. Appl. No. 13/088,072.
Office action dated Nov. 12, 2014 for U.S. Appl. No. 13/500,753.
Office action dated Nov. 16, 2015 for U.S. Appl. No. 14/435,121.
Office action dated Nov. 21, 2014 for U.S. Appl. No. 13/088,072.
Office Action dated Dec. 2, 2016 for U.S. Appl. No. 14/209,964.
Proceedings of the 61st meeting of Japan Society of Home Economics. 2009, vol. 61st, p. 32.
Proceedings of the 65th Annual meeting of the Japan Society of Nutrition and Food Science. 2011, vol. 65th, p. 110.
Rabelo, F. et al., Pro- and anti-inflammatory cytokines in steatosis and steatohepatitis. Obes Surg. Jul. 2010;20(7):906-12. doi: 10.1007/s11695-010-0181-4.
Saebo (Pharma marine, downloaded online on Feb. 27, 2015 from URL:<www.calamarine.com>).
Sawada, et al. [NASH model—role of interleukin-1 receptor]. Nihon Rinsho. Jun. 2006;64(6):1063-70.
Schlemmer, et al. Oestrogen and essential fatty acid supplementation corrects bone loss due to ovariectomy in the female Sprague Dawley rat. Prostaglandins Leukot Essent Fatty Acids. vol. 61, No. 6, 1999, pp. 381-390.
Schmilovitz-Weiss et al. Role of circulating soluble CD40 as an apoptotic marker in liver disease. Apoptosis. Mar. 2004;9(2):205-10.
Sumida, Y. et al., Serum thioredoxin levels as a predictor of steatohepatitis in patients with nonalcoholic fatty liver disease. J Hepatol. Jan. 2003;38(1):32-8.
Tamimi, et al. An apoptosis panel for nonalcoholic steatohepatitis diagnosis. J Hepatol. Jun. 2011;54(6):1224-9. doi: 10.1016/j.jhep.2010.08.023. Epub Feb. 12, 2011.
Tanaka, et al. Highly Purified Eicosapentaenoic Acid Treatment Improves Nonalcoholic Steatohepatitis. Journal of Clinical Gastroenterology, 2008, vol. 42, No. 4, p. 413-418.
Tavares De Almeida, I. et al., Plasma total and free fatty acids composition in human non-alcoholic steatohepatitis. Jun. 2002. 21(3). 219-223.
The Japan Society of Hepatology ed., "NASH • NAFLD no Shinryo Gaido (Guidelines for Diagnosis and Treatment of NASH and NAFLD)", Bunkodo Co., Ltd., Aug. 22, 2006, and its partial translation.
Tirosh, et al. Nutritional lipid-induced oxidative stress leads to mitochondrial dysfunction followed by necrotic death in FaO hepatocytes. Nutrition. Feb. 2009;25(2):200-8. doi: 10.1016/j.nut.2008.07.023. Epub Oct. 22, 2008.
Valva, et al. Apoptosis markers in liver biopsy of nonalcoholic steatohepatitis in pediatric patients. Hum Pathol. Dec. 2008;39(12):1816-22. doi: 10.1016/j.humpath.2008.04.022. Epub Aug. 20, 2008.
Varma, et al. Thrombospondin-1 is an adipokine associated with obesity, adipose inflammation, and insulin resistance. Diabetes. Feb. 2008;57(2):432-9. Epub Dec. 5, 2007.
Varo, et al. Elevated plasma levels of the atherogenic mediator soluble CD40 ligand in diabetic patients: a novel target of thiazolidinediones. Circulation. Jun. 3, 2003;107(21):2664-9. Epub May 12, 2003.
Watanabe, et al. Hepatology Oct. 2004, 428A, 609.
Yener, et al. Plasminogen activator inhibitor-1 and thrombin activatable fibrinolysis inhibitor levels in non-alcoholic steatohepatitis. J Endocrinol Invest. Nov. 2007;30(10):810-9. Abstract only.
Yilmaz, et al. Serum M30 levels: a potential biomarker of severe liver disease in nonalcoholic fatty liver disease and normal aminotransferase levels. Hepatology. Feb. 2009;49(2):697; author reply 697. doi: 10.1002/hep.22691.
Yoneda, et al. Plasma Pentraxin3 is a novel marker for nonalcoholic steatohepatitis (NASH). BMC Gastroenterol. Nov. 14, 2008;8:53. doi: 10.1186/1471-230X-8-53.
Zimmermann, E. et al., C-reactive protein levels in relation to various features of non-alcoholic fatty liver disease among obese patients. J Hepatol. Sep. 2011;55(3):660-5. doi: 10.1016/j.jhep.2010.12.017. Epub Jan. 14, 2011.

(56) References Cited

OTHER PUBLICATIONS

Bauer, et al., Connective tissue growth factor level is increased in patients with liver cirrhosis out is not associated with complications or extent of liver injury. Regulatory peptides. 2012, 179(1-3):10-14.
Epadel Capsules 300—An EPA Preparation, Apr. 2011 (7th Version) with Translation (4 pages).
European Search Report dated Feb. 8, 2017 for EP Application No. 14852793.0.
Florentino, et al., Nonalcoholic fatty liver disease in menopausal women. Arquivos de gastroenterologia. 2013;50(3): p. 180-185.
Montenegro, et al., Gum Arabic: More than an edible emulsifier, products and applications of biopolymers, ISBN: 978-953-51-0226-7, 2012.
Notice of Allowance dated Oct. 18, 2017 for U.S. Appl. No. 14/775,452.
Office Action dated Jan. 13, 2017 for U.S. Appl. No. 14/914,444.
Office Action dated Apr. 5, 2017 for U.S. Appl. No. 14/209,964.
Office Action dated Apr. 19, 2017 for U.S. Appl. No. 14/775,452.
Office Action dated Oct. 5, 2017 for U.S. Appl. No. 14/714,766.
Witt, P.M. et al., The incorporation of marine n-3 PUFA into platelets and adipose tissue in pre- and postmenopausal women: a randomised, double-blind, placebo-controlled trial. British journal of nutrition. 104; 2010: 318-325.

\* cited by examiner

COMPOSITIONS AND METHODS FOR TREATING NON-ALCOHOLIC STEATOHEPATITIS

Cross-Reference

This application is a continuation application of U.S. Application No. 14/435,121 filed Apr. 10, 2015, which is a National Stage Entry of PCT/JP2012/006551 filed Oct. 12, 2012, each of which is incorporated herein by reference in its entirety.

TECHNICAL FIELD

The present invention relates to compositions and methods comprising ethyl icosapentate for treatment of non-alcoholic steatohepatitis (NASH).

BACKGROUND ART

It is known that heavy alcohol use can lead to liver complications, including alcoholic hepatitis which is often characterized by fatty liver and inflammation. Alcoholic hepatitis can ultimately lead to cirrhosis of the liver (scarring) and hardening of the liver tissue.

Individuals that do not consume excessive amounts of alcohol can also be found to have liver disease complications. Non-alcoholic fatty liver disease (NAFLD) is understood to encompass a variety of liver diseases, including steatosis (simple fatty liver), non-alcoholic steatohepatitis (NASH) and advanced scarring of the liver (cirrhosis). NASH has traditionally been diagnosed by means of a liver biopsy to characterize the liver histology, particularly with respect to the characteristics of inflammation, fibrosis and steatosis (fat accumulation). NASH then generally prefers to clinical findings based upon the liver biopsy of a patient with steatohepatitis, combined with the absence of significant alcohol consumption (Neuschwander-Tetri, B. A. and S. H. Caldwell (2003) Hepatology 37(5): 1202-1209). In NASH, fat accumulation is seen in varying degrees of inflammation (hepatitis) and scarring (fibrosis). Patients having NASH are also often characterized by abnormal levels of liver enzymes, such as aspartate aminotransferase (AST, GOT) and alanine aminotransferase (ALT, GPT). However, a clinical diagnosis of NASH still depends upon a liver biopsy to assess the histologic characteristics of the patient's liver, such that histological examination of liver biopsy tissue is often characterized as the "gold-standard" technique for the assessment of liver fibrosis (Neuschwander-Tetri, ibid).

CITATION LIST

Non Patent Literature

Non Patent Literature 1; Hepatology June 2005; 41:1313-1321 "Design and validation of a historical scoring system for nonalcoholic fatty liver disease"

SUMMARY OF INVENTION

Technical Problem

The object of the present invention is to provide the compositions and methods comprising ethyl icosapentate for the treatment or alleviation of non-alcoholic steatohepatitis (NASH), and alleviation of the symptoms associated with NASH.

Solution to Problem

In one embodiment of the invention is that a pharmaceutical agent for treatment or alleviation of symptoms of non-alcoholic steatohepatitis (hereinafter abbreviated as NASH), an effective amount of ethyl icosapentate is administered after determining in a subject a baseline level indicative of NASH of at least one criteria selected from the group consisting of NAS score, steatosis score, lobular inflammation score, ballooning score and fibrosis stage.

In (1) embodiment of the invention Ethyl icosapentate for use in the treatment or alleviation of symptoms of NASH in a subject in need thereof, wherein:

(a) a baseline level in a subject having NASH of at least one criteria selected from the group consisting of NAS score, steatosis score, lobular inflammation score, ballooning score and fibrosis stage is determined; and (b) an effective amount of ethyl icosapentate (EPA-E) is administered to said subject.

(2) The ethyl icosapentate for use of (1), wherein said subject has a NAS score of 4 or more than 4.

(3) The ethyl icosapentate for use (1) or (2), wherein said subject is characterized by at least one criteria selected from the group consisting of a baseline ALT value of 10 to 300 U/L; a baseline AST value of 10 to 250 U/L; a baseline steatosis grade of 2 to 3; and a baseline lobular inflammation grade of 2 to 3.

(4) The ethyl icosapentate for use of any one of (1) to (3), wherein after said administration of said EPA-E for about one year, said subject exhibits at least one improvement selected from the group consisting of a reduced ALT value as compared to said baseline ALT value; a reduced AST value as compared to said baseline AST value; a reduced steatosis grade as compared to said baseline steatosis grade; and a reduced lobular inflammation grade as compared to said baseline lobular inflammation grade.

(5) The ethyl icosapentate for use of any one of (1) to (4), wherein said ethyl icosapentate is administered to said subject in an amount of between 300 to 4000 mg per day.

(6) The ethyl icosapentate for use of any one of (1) to (5), wherein said subject is further characterized by having at least one condition selected from the group consisting of high TG, low HDL-C, diabetes, impaired glucose tolerance and metabolic syndrome.

(7) The ethyl icosapentate for use of any one of (4) to (6), wherein said reduced ALT value is at least 5% lower than said baseline ALT value and/or said reduced AST value is at least 5% lower than said baseline AST value.

(8) The ethyl icosapentate for use of any one of (1) to (7), further comprising determining in said subject prior to treatment a baseline level in serum of at least one member selected from the group consisting of ALT in a range of 10 to 300 U/L, AST in a range of 10 to 250 U/L, HDL-C in a range of 25 to 55 mg/dl, LDL-C in a range of 100 to 200 mg/dl, triglycerides in a range of 100 to 1000 mg/dl, TC in a range of 170 to 300 mg/dl, High TG and low HDL-C, TG/HDL-C ratio in a range of 3.75 to 10, non-HDL-C in a range of 100 to 250 mg/dl, Free fatty acid in a range of 400 to 1000 micro Eq/L, HOMA-IR in a range of 1.5 to 5, HbA1c in a range of 5.7 to 10%, Fasting plasma glucose in a range of 100 to 200 mg/dl.

(9) The ethyl icosapentate for use of any one of (1) to (8), wherein after administration of ethyl icosapentate for at least 3 months, said subject exhibits the following changes in said at least one marker as compared to the baseline level of at least 1% reduction for ALT, AST, TG, TG/HDL ratio, Free fatty acid, AA, MUFA, Palmitoleic acid, Oleic acid, Oleic acid/Stearic acid ratio, Palmitoleic acid/Palmitic acid ratio, Adrenic acid/AA ratio, Ferritin, Thioredoxin, TNF-alpha, sTNF-R1, sTNF-R2, Hs-CRP, CRGF, sCD40, Leptin, complement factor D, CK18 fragment, serum HMGB1, soluble Fas antigen, Hyaluronic acid, Type IV collagen (7s domain), procollagen III peptide or PAI-1; at least 5% increase for EPA or EPA/AA ratio; at least 1% increase for DPA, AA/Homo-gamma-linolenic acid ratio or Serum adiponectin; no worsening of ALP, bilirubin, GGT, Albumin, HDL-C, LDL-C, TC, non-HDL-C, HOMA-IR, HbA1c, Glucose, Fasting plasma glucose, postprandial plasma glucose, OGTT, platelet count or BMI.

(10) The ethyl icosapentate for use of any one of (1) to (9), wherein: the NAS score in said subject after administering (i) to a composite score of 3 or less than 3 and no worsening of said fibrosis stage score, or (ii) by 2 or more than 2 across at least two of the NAS components and no worsening of said fibrosis stage score is improved.

In another embodiment of the invention the ethyl icosapentate for use in the treatment or alleviation of symptoms of NASH, wherein an effective amount of ethyl icosapentate is administered to a subject for treating NASH after identifying the subject having NASH; determining the baseline level in the subject of at least one criteria selected from the group consisting of NAS score, steatosis score, lobular inflammation score, ballooning score and fibrosis stage.

In another embodiment of the invention ethyl icosapentate for use in the treatment or alleviation of symptoms of NASH, wherein a subject/patient having NASH is identified after determining the baseline level in the subject of at least one criteria selected from the group consisting of NAS score, steatosis score, lobular inflammation score, ballooning score and fibrosis stage; administering to the subject an effective amount of ethyl icosapentate; and improving the NAS score (i) to a composite score of less than 3 or equal to 3 or (ii) by 2 across at least two of the NAS components, combined with no worsening of the fibrosis stage score.

In another embodiment of the invention the ethyl icosapentate for use in treatment or alleviation of symptoms NASH, wherein the identification is a subject having NASH characterized by baseline levels of ALT of between 5 to 300 U/L and at least one criteria selected from the group consisting of NAS score of 4 or more than 4, a steatosis score of 1 or more than 1, a lobular inflammation score of 1 or more than 1 and either (i) a fibrosis stage of at least 1a or (ii) ballooning; administering to the subject an effective amount of ethyl icosapentate; and improving the NAS score in the subject (i) to a composite score of 3 or less than 3 or (ii) by 2 or more than 2 across at least two of the NAS components, together with no worsening of the fibrosis stage score.

In another embodiment of the invention, the ethyl icosapentate for use in treatment or alleviation of symptoms NASH, wherein;
a subject is identified having NASH characterized by baseline levels of ALT of between 5 to 300 U/L and at least one criteria selected from the group consisting of NAS score of 4 or more than 4, a steatosis score of 1 or more than 1, a lobular inflammation score of 1 or more than 1 and either (i) a fibrosis stage of at least 1a or (ii) ballooning, and at least one or any combination of two or more of the pretreatment baseline of the items mentioned in Tables 1 and 2;
a baseline level in blood or physical condition prior to treatment in the subject is determined;
an effective amount of ethyl icosapentate is administered to the subject; and the NAS score in the subject (i) to a composite score of 3 or less than 3, or (ii) by 2 or more than 2 across at least two of the NAS components, together with no worsening of the fibrosis stage score, optionally improving at least one selected from the items mentioned in Tables 1 and 2 is improved.

In another embodiment of the invention, the ethyl icosapentate for use in treatment or alleviation of symptoms NASH, wherein the subject is taking at least one drug selected from the group consisting of lipid-lowering drugs, HMG-CoA reductase inhibitors (stains), fibrates, probucol, ezetimibe, ursodiol (UDCA), taurine, betaine, N-acetylcysteine, s-adenosylmethionine (SAM-e), milk thistle, anti-TUMOR NECROSIS FACTOR (TNF) therapies, probiotics, anti-diabetic medications, biguanides (metformin), insulin, sulfonylureas, alpha-glucosidase inhibitors (acarbose), dipeptidyl-peptidase 4 inhibitors (sitagliptin, saxagliptin, alogliptin, vildagliptin, linagliptin, etc.), phenylalanine derivatives (nateglinide, repaglinide), anti-platelet therapy, anti-thrombotic agents, Glucagon-like peptide-1 (GLP-1) receptor agonists (liraglutide, exenatide, taspoglutide, etc.), PDE-4 inhibitor, angiotensin II-1 type receptor antagonist (ARB: losartan, etc.), polyenephosphatidylcholine, antioxidant (vitamine E, vitamin C, nicotinic acid tocopherol, etc.), and pentoxifylline.

In another embodiment of the invention, ethyl icosapentate for use in the treatment or alleviation of symptoms of NASH wherein,
a subject is identifyed having NASH characterized by baseline levels of ALT of between 5 to 300 U/L and at least one criteria selected from the group consisting of NAS score of 4 or more than 4, a steatosis score of 1 or more than 1, a lobular inflammation score of 1 or more than 1 and either (i) a fibrosis stage of at least 1a or (ii) ballooning, and at least one or any combination of two or more of the pretreatment baseline of the items mentioned in Tables 1 and 2;
a baseline level in blood or physical condition prior to treatment in the subject is determined;
an effective amount of ethyl icosapentate administering to the subject in combination with at least one drug selected from the group consisting of lipid-lowering drugs, HMG-CoA reductase inhibitors (stains), fibrates, probucol, ezetimibe, ursodiol (UDCA), taurine, betaine, N-acetylcysteine, s-adenosylmethionine (SAM-e), milk thistle, anti-TNF therapies, probiotics, anti-diabetic medications: biguanides (metformin), insulin, sulfonylureas, alpha-glucosidase inhibitors (acarbose), dipeptidyl-peptidase 4 inhibitors (sitagliptin, saxagliptin, alogliptin, vildagliptin, linagliptin, etc.), phenylalanine derivatives (nateglinide, repaglinide), anti-platelet therapy, anti-thrombotic agents, Glucagon-like peptide-1 (GLP-1) receptor agonists (liraglutide, exenatide, taspoglutide, etc.), PDE-4 inhibitor, angiotensin II-1 type receptor antagonist (ARB: losartan, etc.), polyenephosphatidylcholine, antioxidant (vitamine E, vitamin C, nicotinic acid tocopherol, etc.), and pentoxifylline; and
the NAS score in the subject is improved (i) to a composite score of 3 or less than 3, or (ii) by 2 or more than 2 across at least two of the NAS components, together with no worsening of the fibrosis stage score, optionally improving at least one of items mentioned in Tables 1 and 2.

In a further embodiment of the invention, ethyl icosapentate for use in the treatment or alleviation of symptoms of NASH wherein a subject an effective amount of ethyl icosapentate is administered, the subject has NASH characterized by baseline levels of ALT of between 5 to 300 U/L and at least one criteria selected from the group consisting of a NAS score of 4 or more than 4, a steatosis score of 1 or more than 1, lobular inflammation score of 1 or more than 1 and either (i) a fibrosis stage of at least 1a or (ii) ballooning; and the NAS score in the subject (i) to a composite score of 3 or less than 3, or (ii) by 2 or more than 2 across at least two of the NAS components, together with no worsening of the fibrosis stage score is improved.

In another embodiment of the invention, ethyl icosapentate for use in reducing steatosis, liver lobular inflammation, ballooning and/or liver fibrosis in a subject in need thereof, wherein, an effective amount of ethyl icosapentate (EPA-E) is administered to a subject; at least one condition selected from the group consisting of the steatosis, lobular inflammation, ballooning and liver fibrosis condition of said subject is improved, and no worsening of said fibrosis stage score; and said subject exhibits the following changes in said at least one marker as compared to a baseline pretreatment level of at least 1% reduction for ALT, AST, Triglycerides (TG), TG/HDL-C ratio, Free fatty acid, Arachidonic acid (AA), monounsaturated fatty acid (MUFA), Palmitoleic acid, Oleic acid, Oleic Acid/Stearic acid ratio, Palmitoleic acid/Palmitic acid ratio, Stearic acid/Palmitic acid ratio, gamma-linolenic acid/Linolenic acid ratio, Adrenic acid/AA ratio, Ferritin, Thioredoxin, Tumor necrosis factor-alpha (TNF-alpha), sTNF-R1 (Tumor necrosis factor receptor I, soluble), sTNF-R2 (Tumor necrosis factor receptor II, soluble), Hs-CRP, CTGF, sCD40, Leptin, complement factor D, CK18 fragment, serum HMGB1, soluble Fas antigen, Hyaluronic acid, Type IV collagen (7s domain), procollagen III peptide or PAI-1; at least 5% increase for EPA or EPA/AA ratio; at least 1% increase for DPA, AA/Homo-gamma-linolenic acid ratio or Serum adiponectin; no worsening of ALP, bilirubin, GGT, Albumin, HDL-C, LDL-C, Total Cholesterol (TC), non-HDL-C, HOMA-IR, HbA1c, Fasting plasma glucose, postprandial plasma glucose, OGTT, platelet count or BMI.

In another embodiment of the invention, the ethyl icosapentate for use in reducing steatosis, liver lobular inflammation, ballooning and/or liver fibrosis in a subject in need thereof, wherein;

a baseline level in blood or physical condition prior to treatment in the subject having at least one item or any combination of two or more items selected from the pretreatment baseline of the items mentioned in Tables 1 and 2 is determined;

an effective amount of ethyl icosapentate (EPA-E) is administered to the subject;

at least one condition selected from the group consisting of the steatosis, lobular inflammation, ballooning and liver fibrosis condition of said subject without worsening said fibrosis stage score is improved; and said subject exhibits the described changes in at least one of items mentioned in Tables 1 and 2 as compared to a baseline pre-treatment level of the item.

In another embodiment of the invention, the ethyl icosapentate for use in treatment or alleviation of symptoms NASH, wherein the subject is taking at least one drug selected from the group consisting of lipid-lowering drugs, HMG-CoA reductase inhibitors (stains), fibrates, probucol, ezetimibe, ursodiol (UDCA), taurine, betaine, N-acetylcysteine, s-adenosylmethionine (SAM-e), milk thistle, anti-TNF therapies, probiotics, anti-diabetic medications: biguanides (metformin), insulin, sulfonylureas, alpha-glucosidase inhibitors (acarbose), dipeptidyl-peptidase 4 inhibitors (sitagliptin, saxagliptin, alogliptin, vildagliptin, linagliptin, etc.), phenylalanine derivatives (nateglinide, repaglinide), anti-platelet therapy, anti-thrombotic agents, Glucagon-like peptide-1 (GLP-1) receptor agonists (liraglutide, exenatide, taspoglutide, etc.), PDE-4 inhibitor, angiotensin II-1 type receptor antagonist (ARB: losartan, etc.), polyenephosphatidylcholine, antioxidant (vitamine E, vitamin C, nicotinic acid tocopherol, etc.), and pentoxifylline.

In another embodiment of the invention, ethyl icosapentate for use in the treatment or alleviation of symptoms of NASH wherein an effective amount of ethyl icosapentate is administered to a subject, wherein the subject is possible or definite NASH, and a baseline level in blood or physical condition prior to treatment in the subject of at least one member selected from the group consisting of ALT, AST, AST/ALT ratio, ALP, bilirubin, GGT, Albumin, HDL-C, LDL-C, TG, TC, TG/HDL-C ratio, non-HDL-C, Free fatty acid, AA, EPA, DPA, DHA, EPA/AA ratio, DPA/AA ratio, DHA/AA ratio, DHA/DPA ratio, MUFA, Palmitoleic acid, Oleic acid, Oleic acid/Stearic acid ratio, Palmitoleic acid/Palmitic acid ratio, Stearic acid/Palmitic acid ratio, gamma-linolenic acid/Linolenic acid ratio, AA/Homo-gamma-linolenic acid ratio, Adrenic acid/AA ratio, Ferritin, Thioredoxin, TNF-alpha, sTNF-R1, sTNF-R2, Hs-CRP, CTGF, sCD40, HOMA-IR, HbA1c, Glucose, Fasting plasma glucose, postprandial plasma glucose, OGTT, Leptin, Serum adiponectin, complement factor D, CK18 fragment, serum HMGB1, soluble Fas antigen, Hyaluronic acid, Type IV collagen (7s domain), procollagen III peptide, PAI-1, platelet count or BMI is determined.

In another embodiment of the invention, the ethyl icosapentate for use in the treatment or alleviation of symptoms of NASH, wherein the subject is possible or definite NASH and an effective amount of ethyl icosapentate is administered to a subject, wherein a baseline level in blood or physical condition prior to treatment in the subject of at least one item or any combination of two or more items selected from the items mentioned in Tables 1 and 2 is determined.

In another embodiment of the invention, the ethyl icosapentate for use in treatment or alleviation of symptoms NASH, wherein the subject is possible or definite NASH and the subject is taking at least one drug selected from the group consisting of lipid-lowering drugs, HMG-CoA reductase inhibitors (stains), fibrates, probucol, ezetimibe, ursodiol (UDCA), taurine, betaine, N-acetylcysteine, s-adenosylmethionine (SAM-e), milk thistle, anti-TNF therapies, probiotics, anti-diabetic medications: biguanides (metformin), insulin, sulfonylureas, alpha-glucosidase inhibitors (acarbose), dipeptidyl-peptidase 4 inhibitors (sitagliptin, saxagliptin, alogliptin, vildagliptin, linagliptin, etc.), phenylalanine derivatives (nateglinide, repaglinide), anti-platelet therapy, anti-thrombotic agents, Glucagon-like peptide-1 (GLP-1) receptor agonists (liraglutide, exenatide, taspoglutide, etc.), PDE-4 inhibitor, angiotensin II-1 type receptor antagonist (ARB: losartan, etc.), polyenephosphatidylcholine, antioxidant (vitamine E, vitamin C, nicotinic acid tocopherol, etc.), and pentoxifylline.

In another embodiment of the invention, the ethyl icosapentate for use in the treatment or alleviation of symptoms of NASH wherein an effective amount of ethyl icosapentate is administered to a subject, wherein the subject is possible or definite NASH, and exhibits the following changes in said at least one marker as compared to a baseline pre-treatment level of at least 1% reduction for ALT, AST, TG, TG/HDL-C ratio, Free Fatty acid, AA, MUFA, Palmitoleic acid, Oleic acid, Oleic acid/Stearic acid ratio, Palmitoleic acid/Palmitic acid ratio, Stearic acid/Palmitic acid ratio, gamma-linolenic acid/Linolenic acid ratio, Adrenic acid/AA ratio, Ferritin, Thioredoxin, TNF-alpha, sTNF-R1, sTNF-R2, Hs-CRP, CTGF, sCD40, Leptin, complement factor D, CK18 fragment, serum HMGB1, soluble Fas antigen, Hyaluronic acid, Type IV collagen (7s domain), procollagen III peptide or PAI-1; at least 5% increase for EPA or EPA/AA ratio; at least 1% increase for DPA, AA/Homo-gamma-linolenic acid ratio or Serum adiponectin; no worsening of ALP, bilirubin, GGT, Albumin, HDL-C, LDL-C, TC, non-HDL-C, HOMA-IR, HbA1c, Glucose, Fasting plasma glucose, postprandial plasma glucose, OGTT, platelet count or BMI.

In another embodiment of the invention, the ethyl icosapentate for use in the treatment or alleviation of symptoms of NASH wherein an effective amount of ethyl icosapentate is administered to a subject being possible or definite NASH, and exhibits the described changes of after dosing value in said at least one item selected from the items mentioned in Tables 1 and 2 as compared to a baseline pre-treatment level thereof.

In another embodiment of the invention, the ethyl icosapentate for use in treatment or alleviation of symptoms NASH, wherein the subject is possible or definite NASH and the subject is taking at least one drug selected from the group consisting of lipid-lowering drugs, HMG-CoA reductase inhibitors (stains), fibrates, probucol, ezetimibe, ursodiol (UDCA), taurine, betaine, N-acetylcysteine, s-adenosylmethionine (SAM-e), milk thistle, anti-TNF therapies, probiotics, anti-diabetic medications: biguanides (metformin), insulin, sulfonylureas, alpha-glucosidase inhibitors (acarbose), dipeptidyl-peptidase 4 inhibitors (sitagliptin, saxagliptin, alogliptin, vildagliptin, linagliptin, etc.), phenylalanine derivatives (nateglinide, repaglinide), anti-platelet therapy, anti-thrombotic agents, Glucagon-like peptide-1 (GLP-1) receptor agonists (liraglutide, exenatide, taspoglutide, etc.), PDE-4 inhibitor, angiotensin II-1 type receptor antagonist (ARB: losartan, etc.), polyenephosphatidylcholine, antioxidant (vitamine E, vitamin C, nicotinic acid tocopherol, etc.), and pentoxifylline.

In another embodiment of the invention, the ethyl icosapentate for use in the treatment or alleviation of symptoms of NASH wherein an effective amount of ethyl icosapentate is administered to a subject, wherein the subject is taking at least one drug selected from the group consisting of lipid-lowering drugs, HMG-CoA reductase inhibitors (stains), fibrates, probucol, ezetimibe, ursodiol (UDCA), taurine, betaine, N-acetylcysteine, s-adenosylmethionine (SAM-e), milk thistle, anti-TNF therapies, probiotics, anti-diabetic medications: biguanides (metformin), insulin, sulfonylureas, alpha-glucosidase inhibitors (acarbose), dipeptidyl-peptidase 4 inhibitors (sitagliptin, saxagliptin, alogliptin, vildagliptin, linagliptin, etc.), phenylalanine derivatives (nateglinide, repaglinide), anti-platelet therapy, anti-thrombotic agents, Glucagon-like peptide-1 (GLP-1) receptor agonists (liraglutide, exenatide, taspoglutide, etc.), PDE-4 inhibitor, angiotensin II-1 type receptor antagonist (ARB: losartan, etc.), polyenephosphatidylcholine, antioxidant (vitamine E, vitamin C, nicotinic acid tocopherol, etc.), and pentoxifylline.

In another embodiment of the invention, the ethyl icosapentate for use in the treatment or alleviation of symptoms of NASH wherein an effective amount of ethyl icosapentate is administered to a subject, wherein the subject is taking at least one lipid-lowering drug.

In another embodiment of the invention, the ethyl icosapentate for use in the treatment or alleviation of symptoms of NASH wherein an effective amount of ethyl icosapentate is administered to a subject, wherein the subject is taking an HMG-CoA reductase inhibitor (statins; pravastatin sodium, simvastatin, pitavastatin calcium, atorvastatin calcium hydrate, rosuvastatin calcium, etc.).

In another embodiment of the invention, the ethyl icosapentate for use in the treatment or alleviation of symptoms of NASH wherein an effective amount of ethyl icosapentate is administered to a subject, wherein the subject is taking a Glucagon-like peptide-1 (GLP-1) receptor agonist (liraglutide, exenatide, taspoglutide, etc.).

In another embodiment of the invention, the ethyl icosapentate for use in the treatment or alleviation of symptoms of NASH wherein an effective amount of ethyl icosapentate is administered to a subject in combination with at least one drug selected from the group consisting of lipid-lowering drugs, HMG-CoA reductase inhibitors (stains), fibrates, probucol, ezetimibe, ursodiol (UDCA), taurine, betaine, N-acetylcysteine, s-adenosylmethionine (SAM-e), milk thistle, anti-TNF therapies, probiotics, anti-diabetic medications: biguanides (metformin), insulin, sulfonylureas, alpha-glucosidase inhibitors (acarbose), dipeptidyl-peptidase 4 inhibitors (sitagliptin, saxagliptin, alogliptin, vildagliptin, linagliptin, etc.), phenylalanine derivatives (nateglinide, repaglinide), anti-platelet therapy, anti-thrombotic agents, Glucagon-like peptide-1 (GLP-1) receptor agonists (liraglutide, exenatide, taspoglutide, etc.), PDE-4 inhibitor, angiotensin II-1 type receptor antagonist (ARB: losartan, etc.), polyenephosphatidylcholine, antioxidant (vitamine E, vitamin C, nicotinic acid tocopherol, etc.), and pentoxifylline.

In another embodiment of the invention, the ethyl icosapentate for use in the treatment or alleviation of symptoms of NASH wherein an effective amount of ethyl icosapentate is administered to a subject, wherein the subject is taking an anti-diabetic drug.

In another embodiment of the invention, the ethyl icosapentate for use in the treatment or alleviation of symptoms of NASH wherein an effective amount of ethyl icosapentate is administered to a subject, wherein the subject is not taking any anti-diabetic drugs.

In another embodiment of the invention, the ethyl icosapentate for use in the treatment or alleviation of symptoms of NASH wherein an effective amount of ethyl icosapentate is administered to a subject, wherein the subject is not diabetic.

In another embodiment of the invention, the ethyl icosapentate for use in the treatment or alleviation of symptoms of NASH wherein an effective amount of ethyl icosapentate is administered to a subject, wherein the subject has diabetes.

In another embodiment of the invention, the ethyl icosapentate for use in the treatment or alleviation of symptoms of NASH wherein an effective amount of ethyl icosapentate is administered to a subject, wherein the subject has impaired glucose tolerance.

In another embodiment of the invention, the ethyl icosapentate for use in the treatment or alleviation of symptoms of NASH wherein an effective amount of ethyl icosapentate is administered to a subject, wherein the subject has metabolic syndrome.

In another embodiment of the invention, the ethyl icosapentate for use in reducing at least one marker as compared to a baseline pre-treatment level of Hs-CRP, CTGF, sCD40, Leptin, complement factor D, serum HMGB1, soluble Fas antigen or procollagen III peptide in a subject, comprising administering to a subject an effective amount of ethyl icosapentate (EPA-E), wherein the subject has NASH.

In another embodiment of the invention, the ethyl icosapentate for use in determining efficacy of NASH treatment by (i) administering to a subject an effective amount of EPA-E, (ii) measuring at least one marker of the items mentioned in Tables 1 and 2 during the treatment, (iii) comparing the measured levels of markers to established levels in advance, and optionally (iv) determining whether the treatment is efficacious.

DETAILED DESCRIPTION OF THE INVENTION

The compositions and methods of the present invention are useful for the treatment of NASH by administration of an effective amount of ethyl icosapentate.

Icosapentaenoic acid (EPA) is a known omega-3 polyunsaturated, long-chain fatty acid. Omega-3 fatty acids are known as components of oils, such as fish oil, and a variety of commercial products are promoted as containing omega-3 fatty acids, or their esters, derivatives, conjugates and the like. Icosapentaenoic acid (EPA) is also per se known in its ethyl ester form, ethyl icosapentate (EPA-E). According to the present invention, EPA-E can be administered in a composition. EPA-E content in the total fatty acid of the compositions of the present invention are not particularly limited as long as the composition contains EPA-E as its effective component and intended effects of the present invention are attained; high purity EPA-E is preferably used; for example, the composition having a proportion of the EPA-E of preferably 40% by weight or more, more preferably 90% by weight or more, and still more preferably 96.5% by weight or more in total of the fatty acids and their derivatives. EPA-E can be administered to patients in a highly purified form, including the product known as Epadel (Trade mark) (Mochida Pharmaceutical Co., Ltd., Tokyo Japan). The compositions of EPA-E are administered according to the invention to a subject or patient to provide the patient with a dosage of about 0.3-10 g per day of EPA-E, alternatively 0.6-6 g per day, alternatively 0.9-3.6 g per day or specifically about 300-4000 mg per day or preferably 900-3600 mg per day or more preferably about 1800-2700 mg per day of EPA-E. The compositions of EPA-E are administered according to the invention to a subject or patient preferably one two, or three times per day.

Since EPAs are highly unsaturated, the preparation as described above preferably contains an antioxidant at an amount effective for suppressing oxidation of the EPAs. Exemplary antioxidants include butylated hydroxytoluene (BHT), butylated hydroxyanisole (BHA), propyl gallate, gallic acid, pharmaceutically acceptable quinone, and alpha-tocopherol.

The composition to be administered can contain other fatty acids, especially any omega-3 unsaturated fatty acid, especially DHA-E. The ratio of EPA-E/DHA-E in the composition, the content of EPA-E and DHA-E in the total fatty acids and administration amount of EPA-E and DHA-E are not limited but the ratio is preferably 0.8 or more, more preferably 1.0 or more, still more preferably 1.2 or more. The composition is preferably highly purified; for example, the proportion of EPA-E+DHA-E in the fatty acids and their derivatives is preferably 40% by weight or more, more preferably 80% by weight or more, and still more preferably 90% or more. The daily amount in terms of EPA-E+DHA-E is typically 0.3 to 10.0 g/day, preferably 0.5 to 6.0 g/day, and still more preferably 1.0 to 4.0 g/day. The low content of other long chain saturated fatty acids is preferred, and among the long chain unsaturated fatty acids, the content of omega-6 fatty acids, and in particular, the content of arachidonic acid is preferably as low as less than 2% by weight, and more preferably less than 1% by weight. For example, soft capsule (Lovaza) (Trade mark) or Omacor (Trade mark) containing about 46% by weight of EPA-E and about 38% by weight of DHA-E is commercially available in the U.S., EP and other countries as a therapeutic agent for hyerptriglyceridemia.

Patients treated for NASH can be administered EPA-E according to the invention for 3, 6 or 9 months, or for 1 year or more and can be administered EPA-E in one, two or three dosage per day, or other multiple doses per day including 1 to about 10, 1 to 8, 1 to 6, 1 to 4 or 1 to 2 dosage units per day as appropriate for patient therapy. The term "dose unit" and "dosage unit" herein refer to a portion of a pharmaceutical composition that contains an amount of EPA-E for a single administration to a subject.

While meal affects absorption of the EPA-E, and the administration of the EPA-E is preferably conducted during the meal or after the meal, and more preferably immediately after the meal (within 30 minutes after the meal). The self-emulsifying composition has excellent absorption under fasting, and therefore, it exhibits the intended effects even when administered at a timing other than during, after, or immediately after the meal.

Compositions comprising EPA-E useful for the invention include commercially available compositions of EPA-E, such as Epadel (Trade mark) noted above. Compositions comprising EPA-E may be administered in tablet, capsule, microcapsule, jelly, enteric preparation, extended release preparation, powder or any other solid oral dosage form, as a liquid, emulsion, self-emulsifying composition, as a soft gel capsule or other capsule form, or other appropriate and convenient dosage forms for administration to a patient in need thereof. Compositions can also include pharmaceutically acceptable excipients known to those of ordinary skill in the art including surfactants, oils, co-solvents or combinations of such excipients, together with stabilizers, emulsifiers, preservatives, solubilizers and/or other non-active pharmaceutical ingredients known to those of skill in the art relative to the preparation of pharmaceutical compositions.

1. Evaluation Criteria for Patients

As noted above, the "gold-standard" for a complete diagnosis of NASH involves a liver biopsy. Patients or subjects treated for NASH according to the present invention can also be evaluated for the following criteria, including evaluation prior to initiation of treatment in order to provide a baseline level or score for the criteria as well as evaluation after the dosing regimen to evaluate any improvement in the criteria.

a. NAS Score:

A non-alcoholic fatty liver disease activity score (NAS) is defined as the unweighted sum of the values for steatosis (ranging from 0-3), lobular inflammation (ranging from 0-3) and ballooning (ranging from 0-2), thereby providing a range of NAS score of from 0 to 8. (See Kleinen et al., Design and Validation of a Histological Scoring System for Nonalcoholic Fatty Liver Disease, Hepatology, Vol. 41, No. 6, 2005, pp. 1313-1321) Patients treated for NASH according to the present invention can show a NAS score prior to treatment of 4 or more than 4, with a minimum score of 1 each for steatosis and lobular inflammation plus either ballooning or at least 1a sinusoidal fibrosis and a finding of possible or definite steatohepatitis. After dosing/treatment, such as for one year, patients can show a composite NAS score of 3 or less than 3, 2 or less than 2, or 1 or less than 1, together with no worsening in fibrosis. Alternatively, patients can show an improvement in NAS by a value of 2 or more than 2 across at least two of the NAS components, together with no worsening in fibrosis. Alternatively, patients can show an improvement in NAS score by 3 or more than 3, 4 or more than 4, 5 or more than 5, 6 or more than 6, 7 or more than 7, or 8 or more than 8.

b. Steatosis:

Steatosis is broadly understood to describe a process involving the abnormal retention of lipids within the liver, which accumulation inhibits the normal liver functions. Liver biopsy enables analysis and scoring of steatosis in a patient, with scores ranging from 0-3. Patients treated for NASH according to the present invention can have a steatosis score of 1, 2 or 3, such as between about 2 and about 3. After treatment, it is desired for patients to exhibit no worsening of steatosis, alternatively a reduction of at least 1 in the steatosis score, or a reduction of 2 or 3 in the steatosis score. Steatosis is traditionally graded with a score of 1 indicating the presence of fat droplets in less than 33% of hepatocytes, a score of 2 indicating fat droplets observed in 33-66% of hepatocytes, and a score of 3 indicating observation of fat droplets in greater than 66% of hepato sites. (See Kleinen et al., Design and Validation of a Histological Scoring System for Nonalcoholic Fatty Liver Disease, Hepatology, Vol. 41, No. 6, 2005, pp. 1313-1321)

c. Lobular Inflammation:

Lobular inflammation is also evaluated upon liver biopsy and scored with values of 0-3. (See Kleinen et al., Design and Validation of a Histological Scoring System for Nonalcoholic Fatty Liver Disease, Hepatology, Vol. 41, No. 6, 2005, pp. 1313-1321 Table 1) Patients to be treated for NASH can have lobular inflammation scores of 1, 2 or 3, alternatively ranging between 1 and 2 or 2 and 3. After treatment, patients can have a reduction in lobular inflammation score of at least 1, alternatively a reduction of 2 or 3 in lobular inflammation score, and at least no worsening of the lobular inflammation score.

d. Ballooning:

Ballooning of hepatocytes is generally scored with values of 0-2, (See Kleinen et al., Design and Validation of a Histological Scoring System for Nonalcoholic Fatty Liver Disease, Hepatology, Vol. 41, No. 6, 2005, pp. 1313-1321 Table 1), and patients treated for NASH according to the present invention can have ballooning scores of 0-2, including specific values of 1 or 2, and alternatively a score ranging from 1 to 2. After treatment, patients can show at least no worsening of the ballooning score, alternatively a reduction of at least one value lower in the ballooning score, and alternatively a reduction of two in the value of the ballooning score.

e. Fibrosis Stage

Fibrosis is also evaluated upon liver biopsy and scored with values of 0-4, the scores being defined as: 0 represents no fibrosis, 1 represents perisinusoidal or periportal fibrosis, 1a represents mild, zone 3, perisinusoidal fibrosis; 1b represents moderate zone 3, perisinusoidal fibrosis; 1c represents portal/periportal fibrosis; 2 represents perisinusoidal and portal/periportal fibrosis; 3 represents bridging fibrosis; and 4 represents cirrhosis. (See Kleinen et al., Design and Validation of a Histological Scoring System for Nonalcoholic Fatty Liver Disease, Hepatology, Vol. 41, No. 6, 2005, pp. 1313-1321) Patients treated according to the present invention can have a fibrosis stage score of 0-3, including 0, 1, 1a, 1b, 1c, 2 or 3, and can have a fibrosis stage score of at least 1a. After treatment, patients can have a fibrosis stage score that is at least no worse than the baseline score, and alternatively can have a reduction in the fibrosis stage score of at least one level, alternatively at least two or three levels.

2. Additional Criteria/Markers for Evaluation of Patients

As noted above, while liver biopsy is considered the "gold-standard" for clinical assessment of NASH, the condition can also be accompanied or associated with abnormal levels of liver enzymes and other biological blood components. Therefore, patients treated for NASH according to the present invention can also be evaluated for baseline scores of the following criteria before treatment, and evaluated after treatment for possible changes in those criteria. The evaluated criteria can comprise one or more of the following criteria set forth in Tables 1 and 2.

In the present invention, a biological sample of the patient is collected and used to obtain measurement values. Specific examples of the biological sample include blood, plasma, serum, urine, body fluids, and tissues, but are not limited thereto. The biological sample is preferably blood, plasma or serum. The biological sample is collected from a subject by a known method.

In the present invention, a normal value is measured in accordance with a known measuring method if the normal value is known as one of the blood test indices used to detect NASH, or in accordance with a measuring method following a reference document or the like if a common measuring method for the normal value is not established.

For instance, the normal values shown in Tables 1 and 2, except BMI, can be each measured with a biological sample of either blood, plasma or serum. Fatty acids in blood may be used to measure fatty acids. Table 3 shows a list of some reference documents which recite the particulars of the measurement method.

Unless otherwise specified, the fatty acid amount and the fatty acid composition ratio as used in the present invention may be the amount and the composition ratio of fatty acids in any of the plasma, serum and liver. It is also possible indeed to use the fatty acid amount and the fatty acid composition ratio in a specified fraction, such as LDL or VLDL in the blood. It, however, is desirable to use the amount and the composition ratio of fatty acids in the plasma or the serum because of the simplicity of measurement. Each fatty acid to be employed for the calculation of the fatty acid amount and the fatty acid composition ratio is not particularly limited in unit of amount, that is to say, its amount may be expressed in mole, mole percent, a unit of weight, percent by weight, or the like. The sole unit, and the sole method of calculating fatty acid amount and the fatty acid composition ratios should be used if the evaluation is to be made by the comparison of the fatty acid amount and the fatty acid composition ratio over time. It is particularly desirable to calculate the fatty acid amount and the fatty acid composition ratio from fatty acid amounts expressed in mole percent of the total amount of fatty acids. The weight/volume concentration (e.g., micro g/ml), the mole/volume concentration (e.g., mol/L) or the like may also be used for the calculation.

In this description, the term "plasma fatty acid" refers to a plasma total fatty acid unless otherwise specified. It is also possible to use a plasma free fatty acid for the inventive index for the evaluation of the subject's condition or therapeutic effects. The term "liver fatty acid" refers to a liver total fatty acid unless otherwise specified. A liver free fatty acid may optionally be used.

The fatty acid composition may be determined by any method practicable by a person of ordinary skill in the art of the present invention, while it is particularly preferable to determine the composition according to a usual manner.

TABLE 1

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| ALT (alanine aminotransferase, GPT) (6-41 U/L) | 10-300 | Lower limit range values of 10, 50, 100, 150, or 200, upper limit range values of 100, 150, 200, 250, or 300, ranges of 10-300, 10-200, 10-150, 10-100, 100-200, 2000-3000 | at least 1% lower | 1 to about 95% reduction |
| AST (asparate aminotransferase, GOT) (9-34 U/L) | 10-250 | Lower limit range values of 10, 50, 100, 150, or 200, upper limit range values of 100, 150, 200, 250, or 300, ranges of 10-300, 10-200, 10-150, 10-100, 100-200, 200-300 | at least 1% lower | 1 to about 95% reduction |
| AST/ALT ratio | | upper limit range values of 0.5, 0.7, 0.8, 1, 1.2, 2; ranges of 0.5-2, 0.5-1, 1-2 | | |
| alkaline phosptase (ALP) (80-260 IU/L) | 80-300 | ranges of 50-600 | no worsening | no worsening, 1 to about 90% reduction, 300 IU/L or less, 250 IU/L or less |
| Total bilirubin (0.2-1.2 mg/dL) | High compared to average level of normal subject | | no worsening | no worsening, 1 to about 90% reduction, |
| Gamma-Glutamyl Transferase (GGT or γGTP) (males: 5-60 U/L) | High compared to average level of normal subject | | no worsening | no worsening, 1 to about 90% reduction, 100 U/L or less, 70 U/L or less |
| Albumin (3.8-5.2 g/dl) | Low compared to average level of normal subjects | | no worsening | no worsening, 1 to about 90% increase, ranges of 3-6 g/dl, 3.5-5.5 g/dl |
| HDL-C (high density lipoprotein cholesterol) (35-60-mg/dl) | less than 55 | less than 60 mg/dl, 55, 50, 45, 40, 35, 30, 25, or 25 mg/dl; ranges of 25-55, 30-40 mg/dl, 40-50 mg/dl, 50-60 mg/dl, at least 60 | no worsening, at least 1% increase | no change, 1-90% increase, 40 mg/dl or more |
| LDL-C (low density lipoprotein cholesterol) (50-130 mg/dl) | 100-200 | at least 70 mg/dl, 100, 120, 130 140 150, 170, 190, or 200 or a range of 70-300, 70-250, 70-200, 100-250, 100-200, 130-200, 140-180, 100-130, 130-160, 160-190 | no worsening | no change, 1-90% reduction less than 160 mg/dl, 140, 130, 120, 100, 70 mg/dl |

TABLE 1-continued

| | Pre-treatment baseline | | After dosing (effect) values | |
|---|---|---|---|---|
| Item (Typical Normal Values, Units) | Typical Range(s) | Observable Ranges or Values | Typical Range(s) | Observable Ranges or Values |
| Triglycerides (TG) (fed or fasting, 50-150 mg/dl) | 100-1000 | at least 80 mg/dl, 100, 150, 180, 200, 300, 500, 700, 1000, 1200, or 1500, or less than 150, or a range of 100-2500, 100-1500, 100-1000, 150-500, 200-500, 150-300, 150-200, 200-500 | at least 1% lower | 1 to about 90% reduction, 500 mg/dl or less, 300, 200, 150, 100 mg/dl or less |
| Total Cholesterol (TC) (100-200 mg/dl) | 170-300 | a range of 130-300 mg/dl, 200-220, 220-240, 240-260, or at least 260, or less than 200 mg/dl | no worsening | no change, 1-90% reduction |
| TG and HDL-C | High TG and low HDL-C (ex. TG ≥150 mg/dl and HDL≤40 mg/dl) | TG: at least 150, 200, 500 mg/dl HDL-C; less than 40, 50 mg/dl | no worsening | |
| TG/HDL-C ratio | at least 3.75 | at least 2, 2.5, 3, 3.75, 4, 5, 10, or ranges of 2-3.75, 3.75-10 | at least 1% lower | no worsening, at least 1% lower, or 1-90% reduction |
| Non-HDL-C (mg/dl) | at least 130 | at least 100 mg/dl, 130, 150, 160, 170, 190, a range of 100 to 250 | no worsening | no worsening, or at least 1% lower, or less than 130 mg/dl, 150, 160, 170, 190 |
| Free fatty acid (μEq/l) (140-850) | at least 400 | less than 400, at least 400, 600, 800, 1000 | at least 1% lower | no change, or at least 1 to 90% reduction |
| Eicosapentaenoic Acid/Arachidonic Acid (EPA/AA) (ex. (mol/%)/(mol/%) | less than 0.5/ low compared to average level or normal subjects | less than 1, 0.75, 0.5, 0.1, ranges of 0.01-2 | at least 5% increase | 5 to about 200% increase, about 2-200-fold increase |
| Arachidonic Acid (AA) (ex. mol/%) | High compared to average level of normal subjects | | at least 1% lower | no change, 1 to about 90% reduction |
| Eicosapentaenoic Acid (EPA) (ex. mol/%) | low compared to average level of normal subjects | | at least 5% increase | 5 to about 200% increase, about 2-500-fold increase |
| Docosapentaenoic Acid (DPA) (ex. mol/%) | low compared to average level of normal subjects | | at least 1% increase | 1 to about 95% increase |
| Docosahexaenoic Acid (DHA) (ex. mol/%) | low compared to average level of normal subjects | | | |
| DPA/AA ratio | low compared to average level of normal subjects | | | |
| DPA/AA ratio | low compared to average level of normal subjects | | | |

TABLE 1-continued

| | Pre-treatment baseline | | After dosing (effect) values | |
|---|---|---|---|---|
| Item (Typical Normal Values, Units) | Typical Range(s) | Observable Ranges or Values | Typical Range(s) | Observable Ranges or Values |
| DHA/DPA ratio | low compared to average level of normal subjects | | | |
| Monounsaturated fatty acid (MUFA) (ex. mol/%) | High compared to average level of normal subjects | | at least 1% lower | no change, at least 1% lower |
| Palmitoleic acid (16:1 n7) (ex. mol/%) | High compared to average level of normal subjects | | at least 1% lower | no change, at least 1% lower |
| Oleic acid (18:1 n9) (ex. mol/%) | High compared to average level of normal subjects | | at least 1% lower | no change, a least 1% lower |
| Oleic acid (18:1 n9)/ stearic acid (18:0) ratio | High compared to average level of normal subjects | | at least 1% lower | no change, at least 1% lower |
| Palmitoleic acid (16:1)/ Palmitic acid (16:0) ratio | High compared to average level of normal subjects | | at least 1% lower | no change, at least 1% lower |
| Stearic acid (18:0)/ Palmitic acid (16:0) ratio | High compared to average level or normal subjects | | no change, or at least 1% lower | no change, or at least 1% lower |
| γ-linolenic acid(18:3 n6)/ Linolenic acid (18:2 n6) ratio | High compared to average level subjects | | no change, or at least 1% lower | no change, or at least 1% lower |
| AA/Homo-γ-linolenic acid (20:3 n6) ratio | low compared to average level of normal subjects | | no change, or at least 1% increase | no change, or at least 1% increase |
| Acrenic acid (22:4 n6)/ AA ratio | High compared to average level of normal subjects | | no change, or at least 1% lower | no change, or at least 1% lower |
| Ferritin (ng/mL) | | at least 100, 120, 150, 200, 250, 300, 350, 400, or 500 | at least 1% lower | at least 1 to about 95% lower |
| Thioredoxin (ng/mL) | | at least 15, 20, 25, 30, 35, 40, 45, or 50 | at least 1% lower | at least 1 to about 95% lower |
| TNFα (Tumor necrosis factor-α)(pg/mL) (1.79 or less) | at least 1.5 | at least 1, 1.5, 1.6, 1.7, 1.79, 1.8, 1.9, 2.0, 2.2, 2.5, 3, 3.5, 4, 5, 6, 7 or 10 | at least 1% lower | at least 1 to about 95% lower |
| sTNF-R1 (Tumor necrosis factor receptor I, soluble) (pg/mL) | | at least 400, 500, 600, 700, 800, 900, 1000, 1100, 1200, 1500, or 2000 | at least 1% lower | at least 1 to about 95% lower |
| sTNF-R2 (Tumor necrosis factor receptor II, soluble) (pg/mL) | | at least 500, 700, 1000, 1200, 1500, 1700, 2000, 2200, 2500, 2700, or 3000 | at least 1% lower | at least 1 to about 95% lower |

TABLE 1-continued

|  | Pre-treatment baseline | | After dosing (effect) values | |
|---|---|---|---|---|
| Item (Typical Normal Values, Units) | Typical Range(s) | Observable Ranges or Values | Typical Range(s) | Observable Ranges or Values |
| High Sensitivity C-reactive protien (Hs-CRP, mg/dl) | 0.2 | 0.1 or more, 0.2, 0.3, 0.4, 0.5 or more, ranges of 0.1-1, 0.1-0.8, 0.1-0.5, 0.2-0.5 | at least 1% lower | at least 5 to about 95% lower |
| Connective Tissue Growth Factor (CTGF) | High compared to average level of normal subject | | at least 1% lower | at least 5 to about 95% lower |
| Serum Soluble CD40 (sCD40, pg/ml) | | 5 pg/ml or more, 10, 20, 30, 50, 70, 100, 120, 150, 170, 200, 220, 250, 300, 350, 400, 450, 500 or more | at least 1% lower | at least 5 to about 95% lower |
| Insulin resistance Index (HOMA-IR) (1.6 or less) | 1.5 or more | 1.6 or less/1.5 or more, 1.6, 2, 2.5, 3, 3.5, 4 | no worsening | no change, at least 1 to about 50% lower |
| Glycated hemoglobin (HbA1c) (4.3-5.8%) | 5.7 or more | a range of 4.3-5.8, 5.7-6.4, 5.8-6.5, 6.5-7.0, 7.0-8.0/ 5.7 or more, 5.8, 6, 6.5, 7, 7.5, 8, or 8.5 | no worsening | no change, at least 1 to about 50% lower |
| Fasting plasma glucose (FPG) (mg/dl) (less than 100) | 100 or more | less than 100/ 100 or more, 110, 120, 126, 130, 150, 200, 250, 300/ ranges of 100-110, 100-126 | no worsening | no change, or at least 1 to about 50% lower |
| Postprandial plasma glucose (after a meal) | 140 or more | less than 140, 160, 200/ 140 or more, 170, 180, 200, 250, 300, 350 400/ranges of 140-200, 140-170, 170-200 | no worsening | no change, or at least 1 to about 50% lower |
| two-hour glucose levels on the 75-g oral glucose tolerance test (mg/dl) (OGTT) | 140-200 | less than 140, 160, 200/140 or more, 170, 180, 200, 250, 300, 350, 400/ ranges of 140-200, 140-170, 170-200 | no worsening | no change, or at least 1 to about 50% lower |
| Leptin (ng/ml) | | 5 ng/ml or more, 10, 12, 15, 17, 20, 22, 25, 30, 35, 40 or more | at least 1% lower | at least 1 to about 95% reduction |
| Serum adiponectin (µg/mL) | | 5 µg/mL or less, 4.5, 4, 3.5, or 3 µg/mL or less | at least 1% increase | no change, at least 1 to about 95% increase |
| complement factor D | High compared to average level of normal subject | | at least 15% lower | at least 1 to about 95% reduction |
| CK18 fragment | High compared to average level of normal subject | | at least 1% lower | at least 1 to about 95% reduction |

TABLE 1-continued

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| serum High mobility group box 1 protein (HMGB1) | High compared to average level of normal subject | | at least 1% lower | at least 1 to about 95% reduction |
| soluble Fas antigen (CD95, sFas) | High compared to average level of normal subject | | at least 1% lower | at least 1 to about 95% reduction |
| Hyaluronic acid (50 ng/mL or less) | | 25 ng/mL or more, 50, 70, 100, 120, 150, 200, 250, or 300 or more; 200 mL or less, 100, 70, or 50 or less | at least 1% lower | at least 1 to about 95% reduction |
| Type IV collagen (7s domain) (6 ng/mL or less) | | 5 ng/mL or more, 6, 7, 8, 10, 12, 15, or 20 or more; 25 ng/mL or less, 20, 15, 10, or 6 or less | at least 1% lower | at least 1 to about 95% reduction |
| procollagen III peptide 0.3-0.8 U/ml | | 0.2 U/ml or more, 0.3, 0.5, 0.7, 1, 1.2, 1.5, 2, 2.5, 3, 3.5, or 4 or more; 10 or less, 8, 5, 3, 1, or 0.8 or less | at least 1% lower | at least 1 to about 95% reduction |
| PAI-1 (ng/mL) 50 or less | 50 or more | | | |
| platelet count 150000-400000/µL | 150000-300000 | 400000/µL or less, 300000, 200000/a range of 150000-300000 | no change | no change, at least 1% increase |
| BMI | 18.5-40 | 18.5 or more, 20, 25, 30, 35, 40, or 50 or more;/50 or less, 40, 30, 25, 20 or 18.5 or less; or range of 18.5-25, 25-30, 30-35, 35-40 | no change | no change, at least 1% reduction |
| Direct Bilirubin (0-0.4 mg/dl) | High compared to average level of normal subject | | No worsening | No worsening, 1 to about 90% reduction |
| Oleic acid (C18:1 n9)/Palmitic acid (C16:0)ratio | High compared to average level of normal subject | | At least 1% lower | No change, at least 1% lower |
| EPA/AA ratio and Hs-CRP | Low EPA/AA ratio and high Hs-CRP | EPA/AA ratio being 1.0 or less, 0.75, 0.6, 0.5, 0.4, 0.25 or less; Hs-CRP being 0.1 mg/dl or higher, 0.2 mg/dl or higher, 0.3 mg/dl or higher | | EPA/AA ratio increases; Hs-CRP decreases |
| Interleukin-1 receptor antagonist (IL-1 ra) | High compared to average level of normal subject | | at least 1% lower | at least 1 to about 95% lower |
| sPLA2(Secretory phospholipase A2) group II A: type2A, type II A | High compared to average level of normal subject | | at least 1% lower | at least 1 to about 95% lower |

TABLE 1-continued

| | Pre-treatment baseline | | After dosing (effect) values | |
|---|---|---|---|---|
| Item (Typical Normal Values, Units) | Typical Range(s) | Observable Ranges or Values | Typical Range(s) | Observable Ranges or Values |
| sPLA2 activity | Low compared to average level of normal subjects | | No worsening | |
| Interleukin 2(IL-2) | High compared to average level of normal subject | | at least 1% lower | at least 1 to about 95% lower |
| ApolipoproteinA-IV | High compared to average level of normal subject | | at least 1% lower | at least 1 to about 95% lower |
| ApolipoproteinC-II | High compared to average level of normal subject | | at least 1% lower | at least 1 to about 95% lower |
| CCL2: Chemokine(C-C motif) ligand 2 | High compared to average level of normal subject | | at least 1% lower | at least 1 to about 95% lower |
| Thrombospondin 1: TSP1 | High compared to average level of normal subject | | at least 1% lower | at least 1 to about 95% lower |
| IL-3 receptor (Interleukin-3 receptor) alpha chain | High compared to average level of normal subject | | at least 1% lower | at least 1 to about 95% lower |
| Lymphocyte antigen 6 comlex, locus D | High compared to average level of normal subject | | at least 1% lower | at least 1 to about 95% lower |
| MMP12: Matrix metallopeptidase 12 | High compared to average level of normal subject | | at least 1% lower | at least 1 to about 95% lower |
| MMP13: Matrix metallopeptidase 13 | High compared to average level of normal subject | | at least 1% lower | at least 1 to about 95% lower |
| Trehalase (brush-border membrane glycoprotein) | High compared to average level of normal subject | | at least 1% lower | at least 1 to about 95% lower |
| TIMP1: Tissue inhibitor of metalloproteinase 1 | High compared to average level of normal subject | | at least 1% lower | at least 1 to about 95% lower |
| COL1a1: Procollagen type I, alpha 1 | High compared to average level of normal subject | | at least 1% lower | at least 1 to about 95% lower |
| Complement factor D (adipsin) | High compared to average level of normal subject | | at least 1% lower | at least 1 to about 95% lower |
| TNFR (tumor necrosis factor receptor) superfamily, member 19 (TAJ) | High compared to average level of normal subject | | at least 1% lower | at least 1 to about 95% lower |
| TNFAIP (tumor necrosis factor alpha induced protein) 6 | High compared to average level of normal subject | | at least 1% lower | at least 1 to about 95% lower |
| VLDLR (Very low density lipoprotein receptor) | High compared to average level of normal subject | | at least 1% lower | at least 1 to about 95% lower |
| Lipoprotein lipase | High compared to average level of normal subject | | at least 1% lower | at least 1 to about 95% lower |

TABLE 1-continued

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| Ear (Eosinophil associated ribonuclease) A family, members 1,2,3, and 12 | High compared to average level of normal subject | | at least 1% lower | at least 1 to about 95% lower |
| INSL5: Insulin like 5 | Low compared to average level of normal subjects | | At least 1% increase | |
| TGF β2: Transforming growth factor beta 2 | Low compared to average level of normal subjects | | At least 1% increase | |
| HAMP: Hepcidin antimicrobial peptide 1 | Low compared to average level of normal subjects | | At least 1% increase | |
| Lipase member H: LIPH | Low compared to average level of normal subjects | | At least 1% increase | |
| CYP7B1: Cytochrome P450 family 7 subfamily b polypeptide 1 | Low compared to average level of normal subjects | | At least 1% increase | |

TABLE 2

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| 11-HETE (11-hydroxy-5,8,12,14-eicosatetraenoic acid) | High compared to average level of normal subject | | at least 1% lower | at least 1 to about 95% lower |
| Total HEPEs (hydroxyeicosapentaenoic acids)/ total HETEs (Hydroxyeicosatetraenoic Acids) ratio | Low compared to average level of normal subjects | | At least 1% increase | |
| Glycocholate | High compared to average level of normal subject | Twice or more than twice as high as normal subject | at least 1% lower | |
| Taurocholate | High compared to average level of normal subject | Twice or more than twice as high as normal subject | at least 1% lower | |
| Glycocholate/Glycine ratio | High compared to average level of normal subject | Twice or more than twice as high as normal subject | at least 1% lower | |
| Taurocholate/Taurine ratio | High compared to average level of normal subject | Twice or more than twice as high as normal subject | at least 1% lower | |

TABLE 2-continued

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| Total fatty acids of 20 to 24 carbon atoms (C20-24)/total fatty acids of 16 carbon atoms (C16) ratio (ex. μg/ml/μg/ml, wt %/wt %) | Low compared to average level of normal subjects | | At least 1% increase | |
| Total omega-3 polyunsaturated fatty acids of 20 to 24 carbon atoms(C20-24)/ total fatty acids of 16 carbon atoms (C16) ratio (ex. μg/ml/μg/ml, wt %/wt %) | Low compared to average level of normal subjects | | At least 1% increase | |
| Total fatty acids of 20 to 24 carbon atoms(C20-24)/ total fatty acids of 18 carbon atoms (C18) ratio (ex. μg/ml/μg/ml, wt %/wt %) | Low compared to average level of normal subjects | | At least 1% increase | |
| Total omega-3 polyunsaturated fatty acids of 20 to 24 carbon atoms(C20-24)/ total weight of fatty acids of 18 carbon atoms (C18) ratio (ex. μg/ml/μg/ml, wt %/wt %) | Low compared to average level of normal subjects | | At least 1% increase | |
| IL-10(Interleukin-10) | No change or Low compared to average level of normal subjects | | At least 1% increase | |
| Small dense LDL | No change or High compared to average level of normal subjects | at least 20 mg/dl 25, 30, 40, 50, at least 60 mg/dl | at least 1% lower | |
| RLP-TG (Remnant-like lipoprotein particles-triglyceride) | No change or High compared to average level of normal subjects | at least 10 mg/dl, 20, 30, 40, 50, 70, 80, 100, 120, at least 150 mg/dl | at least 1% lower | |
| RLP-C (Remnant-like lipoprotein particles-cholesterol) | No change or High compared to average level of normal subjects | At least 4.5 mg/dl, 5, 5.2, 5.5, 6, 8, 10, 12, at least 15 mg/dl | at least 1% lower, or no change | |
| Whole Blood viscosity (cP/mPa · s) | | High compared to average level of normal subject | at least 1% lower | at least 1% lower |
| Plasma viscosity (cP/mPa · s) | | High compared to average level of normal subject | No worsening | |
| IL-10 (Interleukin-10)/ TNFα ratio | Low compared to average level of normal subject | | At least 1% increase | |

TABLE 2-continued

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| IL-10 (Interleukin-10)/ sCD40 ratio | Low compared to average level of normal subject | | At least 1% increase | |
| Serum adiponectin/ TNFα ratio | Low compared to average level of normal subject | | At least 1% increase | |
| Serum adiponectin/ sCD40 ratio | Low compared to average level of normal subject | | At least 1% increase | |

TABLE 3

| | |
|---|---|
| 11-HETE | Prostaglandins Other Lipid Mediat. 2011 Apr; 94(3-4): 81-7. |
| HETE, HEPE | Analysis of omega-3 and omega-6 fatty acid-derived lipid metabolite formation in human and mouse blood samples. |
| Glycocholate | Metabolism. 2011 Mar; 60(3): 404-13. |
| Taurocholate | Plasma metabolomic profile in nonalcoholic fatty liver disease. |
| IL-10 | Obes Surg. 2010 Jul; 20(7): 906-12. Pro- and anti-inflammatory cytokines in steatosis and steatohepatitis. |
| Small dense LDL | Diabetol Metab Syndr. 2012 Jul 18; 4(1): 34. Fatty liver in men is associated with high serum levels of small, dense low-density lipoprotein cholesterol. |
| RLP-TG | Clinica Chimica Acta 413 (2012) 1077-1086 |
| RLP-C | The characteristics of remnant lipoproteins in the fasting and postprandial plasma. |
| Connective Tissue Growth Factor (CTGF) | Regul Pept. 2012 Sep 4; 179(1-3): 10-14. Connective tissue growth factor level is increased in patients with liver cirrhosis but is not associated with complications or extent of liver injury. |
| Serum Soluble CD40 (sCD40) | Apoptosis 2004; 9: 205-210 Role of circulating soluble CD40 as an apoptotic marker in liver disease. |
| Complement factor D | Int Immunopharmacol. 2009 Nov; 9(12): 1460-3. Serum adipsin levels in patients with seasonal allergic rhinitis: preliminary data. |
| CK18 fragment | Aliment Pharmacol Ther. 2010 Dec; 32(11-12): 1315-22. A new composite model including metabolic syndrome, alanine aminotransferase and cytokeratin-18 for the diagnosis of non-alcoholic steatohepatitis in morbidly obese patients. |
| Serum High mobility group box 1 protein (HMGB1) | PLoS One. 2012; 7(4): e34318. Diagnostic significance of serum HMGB1 in colorectal carcinomas. |
| fatty acid amount and fatty acid composition ratio in blood | Clinical Nutrition (2002) 21 (3) 219-223 Plasma total and free fatty acids composition in human non-alcoholic steatohepatitis. |
| Ferritin, Thioredoxin | J Hepatol. 2003 Jan; 38(1): 32-8. Serum thioredoxin levels as a predictor of steatohepatitis in patients with nonalcoholic fatty liver disease. |
| sTNF-R1, sTNF-R2 | Diabetes Care. 2010 Oct; 33(10): 2244-9. Epub 2010 Jul 27. Association between systemic inflammation and incident diabetes in HIV-infected patients after initiation of antiretroviral therapy. |
| Hs-CRP | J Hepatol. 2011 Sep; 55(3): 660-5. C-reactive protein levels in relation to various features of non-alcoholic fatty liver disease among obese patients. |
| soluble Fas antigen (CD95, sFas) | J Transl Med. 2009 Jul 29; 7: 67. Short term effects of milrinone on biomarkers of necrosis, apoptosis, and inflammation in patients with severe heart failure. |
| Whole Blood viscosity | British Journal of Haematology, 1997 96, 168-173 |
| Plasma viscosity | Blood Viscosity and risk of cardiovascular events: the Edinburgh Artery Study |
| Items in Table1(1-8, 1-9, 1-10) | WO2011/046204 |

EXAMPLE

Treatment of NASH

To evidence the usefulness of the present invention for the treatment of NASH, patients are evaluated for inclusion in the treatment regimen, treated for NASH, and evaluated for effectiveness of the treatment as follows:

Patients are histologically diagnosed with NASH within six months of the initiation of treatment and are willing to submit to a further liver biopsy at the end of the treatment regimen to evaluate effectiveness of the treatment.

1. Inclusion Criteria:

Patients are definitively diagnosed with NASH (via liver biopsy) and exhibit a NAS score of greater than or equal to 4 by a pathologist.

Patients can be of either gender but are greater than 18 years of age.

Patients with diabetes, impaired glucose tolerance or metabolic syndrome that have been on stable dosage of anti-diabetic agents for at least six months prior to the liver biopsy are suitable for treatment.

2. Exclusion Criteria:

Patients may be excluded for treatment based upon an inability or unwillingness to have a liver biopsy for confirming the diagnosis of NASH, having a diagnosis of cirrhosis by pathologist, exhibiting previous bariatric surgery or biliary diversion (i.e. gastric bypass), esophageal banding or gastric banding; serum ALT values of greater than 330 UL, drug use associated with steatohepatitis within 6 months prior to initiation of treatment, such as with corticosteroids, high dose estrogens, methodtrexate, amiodarone, anti-HIV drugs, tamoxifen, or diltiazem; alcohol consumption of greater than 30 g/day, concurrently or for more than three consecutive months within five years prior treatment; a blood alcohol level greater than 0.02% at the time of baseline evaluation; evidence of active substance abuse; including prescription or recreational drugs, the presence of other liver diseases such as acute or chronic hepatitis C, acute or chronic active hepatitis B, Wilson's, autoimmune, alpha1-antitrypsin and hemochromatosis or HIV infection; renal insufficiency; symptomatic coronary; peripheral or neurovascular disease; symptomatic heart failure or advanced respiratory disease requiring oxygen therapy; a history of cerebral or retinal hemorrhage or other bleeding diathesis.

3. Key Criteria for Measuring Baseline and Post Treatment Values:

Patients to be treated are evaluated for one or more of the following criteria.

a) Primary Long-Term Efficacy Outcome Measure

Histology at treatment month 12.5 to evaluate the NAS score, as a comparison to the baseline score measured pre-treatment. (NAS)

b) Primary Short-Term Efficacy Outcome Measure

Change from baseline in ALT levels at Month 3 and Month 6 of treatment.

c) Secondary Efficacy Outcome Measures

Overall NAS score

Feature scores including fibrosis, ballooning degeneration, inflammation and steatosis Liver function tests (AST, alkaline phosphataise, bilirubin, GGT, Albumin)

Cholesterol (including HDL and LDL)

Triglycerides

Fatty acid assay

Ferritin

Thioredoxin

Pro-inflammatory cytokines (TNF-alpha, sTNF-R1, sTNF-R2, Hs-CRP, CTGF, sCD40)

Insulin sensitivity (HOMA-IR)

HbA1c

Glucose

Leptin, Serum adiponectin and complement factor D

CK18 fragment and Serum HMGB1 soluble Fas antigen

Hyaluronic acid

Type IV collagen (7S domain)

Procollagen III peptide d) Safety Outcome Measures

Adverse Events

Hematology/biochemistry/urinalysis

ECG (including QT/QTc measurement)

e) Pharmacokinetic Outcome Measures

EPA, DPA and DHA

Day 1

On Day 1, samples for plasma concentration are obtained at predose and 0.5, 1, 2, 4, 5 and 6 hours after Dose #1 and Dose #3; after Dose #2, samples are obtained at 2, 4, 5 and 6 hours post-dose. After Dose #3, samples are also obtained at 8 and 12 hours post-dose (20 and 24 hours after Dose #1 [prior to the morning dose on Day 2]) $C_{max}$ (Dose #1 and Dose #2s) and $C_{max}$, $T_{max}$, $T_{1/2}$, $AUG_{0-t}$ after third Dose are derived from plasma concentrations Days 29, 85, 169 and 365 (Visits 3, 5, 7 and 9)

A single sample is obtained prior to the morning dose (trough) on Visits 3, 5, 7 and 9.

Css is determined from plasma concentrations

4. Concomitant and Medications:

Particular medications can be prohibited or permitted during treatment according to the invention for NASH.

The following medications can be prohibited during treatment:

Omega-3-acid ethyl esters and omega-3-PUFA containing supplements >200 mg per day Vitamin E>60 IU per day Thiazolidinediones (e.g. pioglitazone, rosiglitazone)

The following medications may be used during the treatment according to the specified restrictions:

Subjects may continue prescription or over-the-counter medications or herbal remedies such as HMG-CoA reductase inhibitors (stains), fibrates, probucol, ezetimibe, ursodiol (UDCA), taurine, betaine, N-acetylcysteine, s-adenosylmethionine (SAM-e), milk thistle, anti-TNF therapies, or probiotics Subjects may continue the following anti-diabetic medications: biguanides (metformin), insulin, sulfonylureas, alpha-glucosidase inhibitors (acarbose), dipeptidyl-peptidase 4 inhibitors (sitagliptin, saxagliptin), and phenylalanine derivatives (nateglinide, repaglinide)

Subjects may continue receiving anti-platelet therapy and anti-thrombotic agents (e.g. warfarin, Aspirin (ASA), and clopidogrel) after study commencement should be monitored closely during the study for bleeding problems.

5. Treatment

Patients are treated with EPA-E comprised of two daily treatments, but the total daily dose of EPA-E being 1800 mg or 2700 mg per day, divided into dosage amounts of 600 mg TID or 900 mg TID, respectively.

Treatment with EPA-E is continued for 12 months.

Patients are periodically evaluated for the selected criteria, such as at month 1, month 3, month 6 and month 12 of treatment.

After 12 months of treatment, patients are evaluated for the criteria noted above, including liver biopsy, NAS score, steatosis, lobular inflammation, ballooning and fibrosis stage, and one or more of the other criteria listed above in Tables 1 and 2.

The invention being thus described, it will be apparent to one of ordinary skill in the art that various modifications of the materials and methods for practicing the invention can be made. Such modifications are to be considered within the scope of the invention as defined by the following claims.

Each of the references from the patent and periodical literature cited herein is hereby expressly incorporated in its entirety by such citation.

The invention claimed is:

1. A method for treating or alleviating non-alcoholic steatohepatitis (NASH), comprising administering to a human subject a self-emulsifying composition that comprises: eicosapentaenoic acid, ethyl eicosapentanoate, or a combination thereof; and an emulsifier,
   wherein the administering results in one or more of:
      an increase of at least 1% to about 95% of serum adiponectin concentration;
      an increase of 1% to about 90% of albumin concentration;
      a reduction of at least 1% to about 50% of glycated hemoglobin (HbA1c) concentration;
      a reduction of 1% to about 90% of alkaline phosphatase (ALP) concentration;
      a reduction of at least 1% to about 95% of Type IV collagen 7S concentration; or
      a reduction of at least 1% to about 95% of hyaluronic acid concentration;
   in the human subject administered with the self-emulsifying composition.

2. The method of claim 1, wherein the administering further results in one or more of:
   at least 1% increase of interleukin-10 (IL-10) concentration;
   at least 1% reduction of small dense LDL concentration; or
   a concentration reduction of at least 1% to about 95% of one or more of:
      interleukin-2 (IL-2);
      interleukin-3 receptor alpha chain;
      apolipoproteinA-IV;
      apolipoproteinC-II;
      chemokine (C-C motif) ligand 2 (CCL2);
      thrombospondin 1 (TSP1);
      lymphocyte antigen 6 complex, locus D;
      matrix metallopeptidase 12 (MMP12);
      matrix metallopeptidase 13 (MMP13);
      trehalase;
      tissue inhibitor of metalloproteinase 1 (TIMP1);
      procollagen type I alpha 1 (COL1A1);
      tumor necrosis factor receptor (TNFR) superfamily member 19;
      tumor necrosis factor alpha induced protein 6 (TNFAIP6);
      very low density lipoprotein receptor (VLDLR);
      lipoprotein lipase;
      eosinophil associated ribonuclease (EAR) A family, member 1;
      EAR A family, member 2;
      EAR A family, member 3; or
      EAR A family, member 12;
   in the human subject administered with the self-emulsifying composition.

3. The method of claim 1, wherein the administering occurs during a meal.

4. The method of claim 1, wherein the administering occurs after a meal.

5. The method of claim 1, wherein the administering occurs within 30 minutes after a meal.

6. The method of claim 1, wherein the administering occurs at a timing other than during, after, or immediately after a meal.

7. The method of claim 1, wherein the human subject is not diabetic.

8. The method of claim 1, wherein the human subject is not taking any anti-diabetic drug.

9. The method of claim 1, wherein the human subject is a possible or definite NASH subject.

10. The method of claim 1, wherein the administering continues for 3, 6, 9, or 12 months.

11. The method of claim 1, wherein the administering provides a dosage of ethyl eicosapentanoate at about 0.3-10 g per day.

12. The method of claim 1, wherein the administering provides a dosage of ethyl eicosapentanoate at 0.6-6 g per day.

13. The method of claim 1, wherein the administering provides a dosage of ethyl eicosapentanoate at 0.9-3.6 g per day.

14. The method of claim 1, wherein the administering provides a dosage of ethyl eicosapentanoate at about 1800-2700 mg per day.

15. The method of claim 1, wherein the administering provides a dosage of ethyl eicosapentanoate at about: 1800 mg or 2700 mg per day.

16. The method of claim 1, wherein the administering provides a dosage of ethyl eicosapentanoate at one, two, or three times per day.

17. The method of claim 1, wherein the administering provides a dosage of ethyl eicosapentanoate at 600 mg or 900 mg three times per day.

18. The method of claim 1, wherein the administering results in an increase of at least 1% to about 95% of serum adiponectin concentration in the human subject.

19. The method of claim 1, wherein the administering results in an increase of 1% to about 90% of albumin concentration in the human subject.

20. The method of claim 1, wherein the administering results in a reduction of at least 1% to about 50% of HbA1c concentration in the human subject.

21. The method of claim 1, wherein the administering results in a reduction of 1% to about 90% of ALP concentration in the human subject.

22. The method of claim 1, wherein the administering results in a reduction of at least 1% to about 95% of Type IV collagen 7S concentration in the human subject.

23. The method of claim 1, wherein the administering results in a reduction of at least 1% to about 95% of hyaluronic acid concentration in the human subject.

* * * * *